United States Patent [19]
Kowalski

[11] Patent Number: 5,939,266
[45] Date of Patent: Aug. 17, 1999

[54] IN VITRO ASSAY FOR ANTICARCINOGENS USING PHENOTYPIC TRANSFORMATION OF HUMAN CELLS

[75] Inventor: Linda A. Kowalski, Vancouver, Canada

[73] Assignee: Viratest Carcinogen Monitoring Ltd., Vancouver, Canada

[21] Appl. No.: 09/042,654

[22] Filed: Mar. 17, 1998

Related U.S. Application Data

[62] Division of application No. 08/696,695, Aug. 14, 1996, Pat. No. 5,763,180.

[51] Int. Cl.$^6$ .............................. C12Q 1/68; C12Q 1/02; C12Q 1/04
[52] U.S. Cl. .................................. 435/6; 435/29; 435/34
[58] Field of Search ................................... 435/6, 29, 34, 435/325

[56] References Cited

U.S. PATENT DOCUMENTS

| | | | |
|---|---|---|---|
| 4,302,535 | 11/1981 | Skopek et al. | 435/6 |
| 4,753,874 | 6/1988 | Calos | 435/6 |
| 4,808,532 | 2/1989 | Stampfer | 435/240 |
| 4,885,238 | 12/1989 | Reddel et al. | 435/29 |
| 4,904,595 | 2/1990 | Gierthy | 435/240 |
| 5,180,666 | 1/1993 | States et al. | 435/29 |
| 5,273,880 | 12/1993 | Schiesti | 435/6 |
| 5,356,806 | 10/1994 | Harris et al. | 435/240.2 |
| 5,384,243 | 1/1995 | Gutkind et al. | 435/6 |
| 5,429,948 | 7/1995 | Crespi et al. | 435/240.2 |
| 5,506,131 | 4/1996 | Harris et al. | 435/240.2 |
| 5,763,180 | 6/1998 | Kowalski | 435/6 |
| 5,837,471 | 11/1998 | Kowalski | 435/6 |

OTHER PUBLICATIONS

Database WPI, Week 8634, Derwent Publications Ltd., London, GB Class BO2, AN–86–221938.
Kakunaga, 1973, *Int. J. Cancer,* 12:463–473.
Molecular Biology of the Cell, second edition, 1989, p. 1201, third paragraph, Garland Publishing, Inc., NY, USA.
Boyer et al., *Cancer Res.,* 50:2593–2598, May, 1990.
Chernova et al., "The Role of p53 in Regulating Genomic Stability when DNA and RNA Synthesis are Inhibited," *TIBS,* 20, Oct. 1995.
Doetsch, *TIBS,* 20:384–386, Oct. 1995.
Greenblatt et al., *Cancer Res.,* 54:4855–4878, Sep. 1994.
Jackson et al., *TIBS,* 20:412–415, Oct. 1995q.
Kastan et al., *Cancer Res.,* 51:6304–6311, Dec. 1991.
Kastan et al., *Cell,* 71:587–597, Nov. 1992.
Kat et al., *Proc. Natl. Acad. Sci. USA,* 90:6424–6428, Jul. 1993.
Lavin et al., "Relationship of the Ataxia–Telangiectasia Protein ATM to Phosphoinositide 3–Kinase", *TIBS,* 20, Oct. 1995.
Leadon et al., *Proc. Natl. Acad. Sci. USA,* 90:10499–10503, Nov. 1993.
Lindahl et al., *TIBS,* 20:405–411, Oct. 1995.
Papadopoulos et al., *Science,* 263:1625–1629, Mar. 1994.
Sancar, *Annu. Rev. Genetics,* 29:69–105, 1995.
Stevnsner et al., 1995, *Carcenogenesis,* 16(11):2855–2858.
Shiloh et al., "In Vitro Phenotype of Ataxia–Telangiectasia (AT) Fibroblast Strains: Clues to the Nature of the 'AT DNA Lesion' and the Molecular Defect in AT", in *Ataxia–Telangiectasia: Genetics, Neuropathology, and Immunology of a Degenerative Disease of Childhood,* pp. 111–121, Alan R. Liss, Inc., 1985.
Stefanini et al., *Am. J. Hum. Genet.,* 53:817–821, 1993.
Steinman et al., *Oncogene,* 9:3389–3396, 1994.
Walker, *TIBS,* 20:416–420, Oct. 1995.

*Primary Examiner*—Nancy Degen
*Attorney, Agent, or Firm*—Sheridan Ross P.C.

[57] ABSTRACT

Disclosed is a method to evaluate the carcinogenicity of a compound using a transformation assay. The method includes contacting a compound to be tested for carcinogenicity with a test cell. The test cell has a defect in a protective cellular mechanism selected from the group of a defect in a DNA damage repair mechanism, a defect in cell cycle control, and a defect in the ability to prevent damage induced by oxygen free radicals. Cell growth is scored to identify the presence or absence of a transformation characteristic. The development of such a transformation characteristic indicates that the compound being tested is carcinogenic. Further embodiments include a method to identify tissue-specific carcinogens, a method to identify the biochemical mechanism of carcinogenicity of a compound, and a method to evaluate the anticarcinogenicity of a compound.

3 Claims, No Drawings

IN VITRO ASSAY FOR ANTICARCINOGENS USING PHENOTYPIC TRANSFORMATION OF HUMAN CELLS

This application is a divisional of U.S. application Ser. No. 08/696,695, filed Aug. 14, 1996, now U.S. Pat. No. 5,763,180, which is incorporated herein by reference in its entirety.

FIELD OF THE INVENTION

The present invention relates to assays for the identification of carcinogenic compounds, and particularly transformation assays and test cells useful therefor.

BACKGROUND OF THE INVENTION

The ability of organisms to prevent cells which have damaged or amplified DNA from replicating, to repair DNA damage, or to terminate cells which have irreparable DNA damage are important defenses against cancer. Cells which have unrepaired mutations and are permitted to divide may form tumors.

Certain human diseases arise from an inherited inability to repair DNA, to prevent DNA damage or to prevent propagation of cells with damaged DNA. As a result, victims have a high rate of cancer. When these cells are contacted by carcinogens, they are unable to repair the DNA damage and the cells are tumorigenically transformed. For example, xeroderma pigmentosum, Cockayne's syndrome and trichothiodystrophy arise from an inability of a cell to perform nucleotide excision repair. These cells are unable to repair damage from alkylating agents and other agents which induce bulky additions to DNA. Fanconi's anemia induces a sensitivity to crosslinking agents such as nitrogen mustard, mitomycin C, and cisplatin. Cells from patients with ataxia-telangiectasia are sensitive to ionizing radiation and to oxidative stress because they are able to continue to divide despite unrepaired DNA damage. Cells from patients with amyotrophic lateral sclerosis are unable to repair oxidative damage caused by active oxygen free radicals because they lack superoxide dismutase. Hereditary nonpolyposis colon cancer occurs as a result of failure of excision repair and mismatch repair.

DNA damage occurs as a result of exposure to mutagens or as a longer term result of exposure to genotoxic or nongenotoxic carcinogens. Mutagenic carcinogens are usually electrophiles or are capable of metabolic conversion to electrophiles which attack DNA causing base alteration and mutation. Nonmutagenic carcinogens induce cell proliferation and DNA synthesis by a variety of biochemical mechanisms eventually resulting in genome alteration; but they are not initially mutagenic. Some metal cations such as vanadate act as mitogens or alter protein phosphorylation.

New chemicals are constantly produced either for consumer use or as by-products into the environment. These potential human carcinogens are tested in cultures of prokaryotes or lower eukaryotes, in living rodents and in mammalian cells in tissue culture. Although these tests are reproducible, reliable, quick, relatively inexpensive and do not sacrifice higher animals, they are inadequate for testing human carcinogens.

Cell transformation assays can detect both mutagenic and nonmutagenic carcinogens. Therefore, presumably, a chemical that induces or promotes transformation is a carcinogen. To investigate chemical carcinogenesis and mechanisms or transformation, several assays have been developed which rely on cell transformation. (See, e.g., DiPaolo, J. A. et al. (1969) "Quantitative Studies of in vitro Transformation by Chemical Carcinogens," *J. Natl. Cancer Inst.*, 42:867; Reznikoff, C. A. et al. (1973) "Establishment and Characterization of a Cloned Line of C3H Mouse Embryo Cells Sensitive to Postconfluence Inhibition of Cell Division," *Cancer Res.* 33:3231; Kakunaga, T. (1973) "A Quantitative System for Assay of Malignant Transformation by Chemical Carcinogens Using a Clone Derived from BALB/c3T3," Intl. *J. Cancer*, 12:463). Transformed foci are the endpoint in these assays.

These tests, however, suffer from lack of reproducibility from laboratory to laboratory, technical difficulties, and difficulties in scoring foci as there are several different types of foci. Due to the low transformation frequency, large numbers of plates must be used to obtain statistically significant results for weak carcinogens. Moreover, these tests do not specifically test for human carcinogens, nor are these prior tests based on the inability of test cells to repair DNA, to prevent DNA damage or to prevent propagation of cells with damaged DNA.

A few assays have been described which can be used to detect potential mutagens in mammalian or specifically, human, cells (See, for example, Calos, 1988, U.S. Pat. No. 4,753,874, Schiestl, 1993, U.S. Pat. No. 5,273,880, Reddel et al., 1989, U.S. Pat. No. 4,885,238, Skopek et al., 1981, U.S. Pat. No. 4,302,535; Harris et al., 1996, U.S. Pat. No. 5,506,131; Crespi et al., 1995, U.S. Pat. No. 5,429,948; and States et al., 1993, U.S. Pat. No. 5,180,666). The assays, however, do not use transformation as an endpoint, but rely on more complex endpoints for detection of carcinogens which are only useful for detecting genotoxic or mutagenic carcinogens. Therefore, the assays described prior to the present invention are not designed to detect non-genotoxic carcinogens and/or tissue-specific carcinogens. These assays also suffer from technical complexity and limited commercial availability. Moreover, these assays do not identify the biochemical mechanism of carcinogenicity of carcinogenic compounds. Therefore, there exists a need for improved transformation assays for rapid and reliable screening for mutagenic, genotoxic, nongenotoxic and tissue-specific carcinogens.

SUMMARY OF THE INVENTION

The present invention relates to a method to evaluate the carcinogenicity of a compound in an in vitro assay. Such a method includes the step of contacting a test cell having a defect in a cellular mechanism for protecting such a cell from transformation with a compound to be tested for carcinogenicity. The method further includes scoring the growth of said test cell based on a transformation characteristic. A positive transformation characteristic indicates that the compound is carcinogenic. In one embodiment, a test cell having a defect in a protective cellular mechanism has a defect selected from the group consisting of a defect in a DNA damage repair mechanism, a defect in cell cycle control, and a defect in the ability to prevent damage induced by oxygen free radicals. Transformation characteristics can include formation of foci, anchorage independence, loss of growth factor or serum requirements, change in cell morphology, ability to form tumors when injected into suitable animal hosts, and/or immortalization of the cell.

In another embodiment, a test cell to be used in an assay of the present invention can be a test cell having a defect in a component involved in a protective cellular mechanism (e.g., a cell having a defect in a tumor suppressor gene). In another embodiment, a test cell to be used in an assay of the present invention is a human cell which is derived from a patient having a disease involving a defect in a protective cellular mechanism. In a preferred embodiment, such a disease includes xeroderma pigmentosum, Cockayne's syndrome, trichothiodystrophy, Fanconi's anemia, ataxia-telangiectasia, hereditary nonpolyposis colon cancer, promyelocytic leukemia, lymphoid leukemia, myeloid leukemia, colorectal carcinoma, amyotrophic lateral sclerosis, Li-Fraumeni syndrome, squamous cell carcinoma and Bloom's Syndrome. In yet another embodiment, a test cell to be used in an assay of the present invention is engineered to have a defect in a protective cellular mechanism.

Another embodiment of the present invention is a method to identify tissue-specific carcinogens. Such method includes the steps of contacting a putative tissue-specific carcinogen with a first test cell of a first tissue-type and also with a second test cell of a second tissue-type, the first test cell and the second test cell having the same defect in a protective cellular mechanism. The method further includes the step of scoring cell growth of the first and second test cell for a transformation characteristic, wherein a positive transformation characteristic in either of the first or second test cells indicates that the compound being tested is carcinogenic. Furthermore, a difference in the magnitude of the transformation characteristic between the first and second test cell indicates that the compound being tested is a tissue-specific carcinogen.

One embodiment of the present invention relates to a method for determining the biochemical mechanism of carcinogenicity of a compound. Such method includes the steps of contacting a putative carcinogen with a first test cell which has a defect in a first protective cellular mechanism, and also with a second test cell which has a defect in a second protective cellular mechanism, wherein the first and second protective cellular mechanisms are different. The method further includes the step of scoring cell growth of the first and second test cell for a transformation characteristic, wherein a positive transformation characteristic in either of the first or second test cells indicates that the compound being tested is carcinogenic. Furthermore, a difference in the magnitude of the transformation characteristic between the first and second test cell indicates that the carcinogen functions within a biochemical pathway that is associated with a specific defect in a protective cellular mechanism.

Yet another embodiment of the present invention is a method to evaluate the carcinogenicity of a compound which includes the steps of contacting a compound to be evaluated with a test cell having a defect in a protective cellular mechanism which is isolated from a patient having a disease selected from xeroderma pigmentosum, Cockayne's syndrome, trichothiodystrophy, Fanconi's anemia, ataxia-telangiectasia, hereditary nonpolyposis colon cancer, promyelocytic leukemia, lymphoid leukemia, myeloid leukemia, colorectal carcinoma, amyotrophic lateral sclerosis, Li-Fraumeni syndrome, squamous cell carcinoma and Bloom's Syndrome. The step of contacting is conducted in the presence of normal cells which do not have such a defect. The method further includes the step of scoring the cells for the formation of foci, which indicates that the compound is carcinogenic.

Another aspect of the present invention includes a method to identify anticarcinogenic compounds. In one embodiment, this method includes contacting a test cell with a compound being tested for anticarcinogenicity. The test cell has a defect in a protective cellular mechanism selected from a defect in a DNA damage repair mechanism, a defect in cell cycle control, and a defect in the ability to prevent damage induced by oxygen free radicals. In one embodiment, the test cell is contacted with the putative anticarcinogenic compound in the presence of a known carcinogen. The method further includes scoring cell growth of the test cell based on identification of a transformation characteristic. The absence of a transformation characteristic indicates that the compound being tested is anticarcinogenic.

In another embodiment of a method to identify anticarcinogenic compounds, the test cell, which has the phenotype of being transformed in the absence of carcinogens, is contacted with the putative anticarcinogenic compound. The absence or reduction of a transformation characteristic indicates that the compound being tested is anticarcinogenic.

DETAILED DESCRIPTION OF THE INVENTION

The present invention generally relates to an in vitro assay for carcinogens which uses phenotypic transformation of test cells as an endpoint. Such an assay involves contacting a compound being tested for carcinogenicity with a test cell having a defect in a cellular mechanism which normally protects a cell from becoming transformed. Such a defect includes a defect in a DNA damage repair mechanism, a defect in cell cycle control, and/or a defect in the ability to prevent damage induced by oxygen free radicals. The method to evaluate the carcinogenicity of a compound further involves identifying whether the compound causes transformation of such test cell having normal growth to a cell having abnormal or altered growth properties. Various aspects of transformed cells and identifying characteristics of transformation are discussed in more detail below.

The method to evaluate the carcinogenicity of a compound has several advantages over previously described assays. A significant advantage of the present invention, because it involves a transformation assay, is that it is capable of identifying nongenotoxic carcinogens as well as genotoxic carcinogens. For example, the well-known Ames test only detects genotoxic carcinogens (e.g., mutagens). One option for identifying non-genotoxic carcinogens is by animal testing. However, animal testing is relatively expensive and time-consuming.

The assay of the present invention also has the advantages over prior assays of being simple, sensitive, having short incubation times, and easily scored endpoints. The methods of evaluating carcinogens disclosed herein are particularly useful for detecting human carcinogens. More particularly, the methods disclosed herein are useful for identifying the biochemical mechanisms of the carcinogenic activity of a particular compound, because such methods comprise test cells which carry particular defects in protective cellular mechanisms, such as those present in many disease states. Another advantage of the assay of the present invention is that tissue-specific carcinogens can be identified.

The method of the present invention provides a test cell having an enhanced transformation response in the presence of carcinogens compared to normal or wild-type cells. Such a test cell has a defect in a protective cellular mechanism. A protective cellular mechanism, as used herein, is a cellular process capable of protecting a cell from becoming transformed. According to the present invention, such a cellular mechanism includes a DNA damage repair mechanism, a cell cycle control mechanism, and/or a mechanism involved in the ability to prevent damage induced by oxygen free radicals. As such, a defect in a test cell of the present invention comprises a defect in at least one of the above mentioned protective cellular mechanisms. Examples of such protective cellular mechanisms are described in detail below.

As used herein, the terms "defect" or "defective" refer to an abnormality or a deficiency within a protective cellular mechanism as described herein. Such a defect causes a cell to be more susceptible to transformation when the cell is exposed to a carcinogen than a cell not having the defect (i.e., a normal, or wild-type cell). In one embodiment, a defect in a test cell of the present invention can be a defective component within a protective cellular mechanism. Such a component can include, for example, a protein or a nucleic acid molecule involved in a protective cellular process such as DNA repair, transcription, tumor suppression, cell cycle control, response to reactive oxygen species (e.g. oxygen free radicals), and apoptosis.

A defective component can be, for example, a protein in which amino acids have been deleted, inserted, inverted, substituted and/or derivatized (e.g., by glycosylation, phosphor lation, acetylation, myristylation, prenylation, palmitoylation, amidation and/or addition of glycerophosphatidyl inositol), such that the protein is incapable of performing its function within a cell, and therefore renders such cell susceptible to transformation. A defective component can also be a nucleic acid molecule in which nucleotides have been inserted, deleted, substituted, and/or inverted, such that the protein encoded by such nucleic acid molecule is not transcribed, is not translated, or altered such that the protein is unable to perform its function within a cell and therefore renders such cell susceptible to transformation.

As used herein, a cell is considered to be transformed when, after it has been subjected to a carcinogenic agent in cell culture, it has developed aberrant growth properties or characteristics. As used herein, the term "carcinogen" is a compound (e.g., a chemical, a protein, a molecule) which causes a cell to demonstrate transformation characteristics in a transformation assay of the present invention. Such transformation characteristics can include any properties associated with tumor or cancer cells. In particular, such characteristics can include formation of foci, anchorage independence, loss of growth factor or serum requirements, change in cell morphology, ability to form tumors when injected into suitable animal hosts, and/or immortalization of the cell. The presence of one or more of such transformation characteristics is indicative that the compound being tested is carcinogenic. In a preferred embodiment of the present invention, such a transformation characteristic is the formation of foci.

One transformation characteristic is when a cell, which normally does not form a focus, forms a focus when grown on a culture dish. Such cells, when not transformed, typically grow in a flat and organized pattern until they cover the surface of a Petri plate with liquid medium on top of them. Then, when each cell is touching its neighbor cell, cell growth stops by virtue of a phenomenon known as contact inhibition. Such cells, when transformed, are not contact inhibited and will grow to high densities in disorganized foci.

A further transformation characteristic which is indicative of a cell being transformed by a carcinogenic compound is anchorage independence. When anchorage independence is the transformation characteristic being used in a particular assay, the cells used in the assay are cells which, when not transformed, are anchorage dependent. That is, when such cells are not transformed, they grow only when attached to a solid surface. Upon becoming transformed, such cells will grow in a medium (e.g. semi-solid agar) without being attached to a solid surface.

A further transformation characteristic which is useful in assays of the present invention is the loss of growth factor or serum requirements. Cells used in assays of the present invention in which loss of growth factor or serum requirements is the transformation characteristic, when not transformed, require the presence of isolated growth factors or serum for growth. Upon transformation, such cells are able to grow in a decreased concentration or absence of the growth factors or serum required by the untransformed cells.

Another transformation characteristic is when a cell, upon transformation, exhibits a change in cell morphology. A change in morphology refers to a change in the structure or shape of the cell as compared to the cell when it is not transformed. Such a change can be observed visually, such as by examining the cells with the aid of a microscope.

A further transformation characteristic which is useful in an assay of the present invention is the ability of a cell to form tumors when injected into suitable animal hosts. When this ability to form tumors is the transformation characteristic, such cells, when not transformed, will not form tumors when injected into animal hosts.

Yet another transformation characteristic is immortalization of a cell. A transformed cell which has the characteristic of being "immortalized" is capable of proliferating indefinitely in long-term culture in the presence of appropriate nutrients and growth factors. That is, when the cell is not transformed, it has a limited life span in culture and eventually dies.

In one embodiment of the present invention, a test cell has a defect in a DNA repair mechanism. A DNA repair mechanism refers to a variety of cellular mechanisms that effect the repair of DNA damage caused by extrinsic or intrinsic agents. For instance, DNA damage can be induced by factors such as UV light, ionizing radiation, reactive oxygen species and electrophilic alkylating agents. As such, a test cell of the present invention can have a defect in the ability to repair DNA damage that is induced by such factors. As used herein, DNA damage can also be referred to as a lesion (e.g. abnormal or modified bases, such as bases damaged by alkylation, oxidation, reduction or fragmentation).

According to the present invention, DNA repair is accomplished by a variety of mechanisms which include, but are not limited to, direct DNA repair, base excision repair, nucleotide excision repair, nucleotide mismatch repair, post-replication repair, cross-link repair, double-strand break repair, and transcription repair.

Direct DNA repair refers to the process by which the chemical bonds that comprise a lesion or connect a modifying agent (e.g. an alkyl group) to the DNA are broken. Base excision repair refers to the process by which a defective base is removed by a glycosylase and the resulting abasic site is removed and replaced with a normal base. Nucleotide excision repair refers to the process by which a lesion is removed by dual excision on either side of the lesion, followed by repair of the resulting gap in the DNA. Nucleotide mismatch repair refers to the process by which improper nucleotide base-pairings (e.g. an adenine paired with a guanine) are corrected. Post-replication repair is a process by which a cell allows completion of replication without directly eliminating a DNA lesion. Such post-replication repair can occur by translesion synthesis, template switching and/or recombination. Cross-link repair refers to the elimination of DNA interstrand cross-links by dual incisions to release the cross-link, followed either by strand transfer and ligation, or by filling of the gap by DNA polymerase involving a three strand intermediate. Double-strand break repair is a process whereby breaks occurring in both DNA strands are repaired by a variety of complex reactions which can include recombination events. Transcription repair can occur during all phases of transcription, including activation, initiation, and/or elongation, utilizing a variety of enzymes and proteins to effect the repair.

Test cells of the present invention having a defect in a DNA repair mechanism can have a defect in any of the above-mentioned DNA repair processes, including a defect in any component which is involved in such DNA repair process. More particularly, a test cell of the present invention can have a defect in a protein selected from the group of Ku80, DNA-$PK_{CS}$, $O^6$-methylguanine-DNA methyltransferase, uracil DNA glycosylase, hydroxymethyluracil DNA glycosylase, thymine glycol DNA glycosylase, N-methylpurine DNA glycosylase, 8-hydroxyguanine DNA glycosylase, AP endonuclease, DNA Polβ, DNA Polε, DNA Polδ, poly (ADP-ribose) polymerase, XPA, p89/XPB-ERCC3, p80/XPD-ERCC2, p62(TFB1), p44/hssL1, p41/cdk7, p38/cyclinH, p34, XPC(p125), HHRA D23(p58), XPF, ERCC1(p33), XPG(p160), p70, p11, AP-1, NFκB, RNA PolI, RNA PolII, hMLH1, hMSH2, DHFR, HPRT, CSA, and CSB, and/or genes corresponding thereto.

Test cells of the present invention having a defect in a DNA repair mechanism are known in the art and include, but are not limited to, cell lines selected from the group of TTD1BR, NIGMS GM739, TK6, MT1, NIGMS GM5509A, NIGMS GM2359, ATCC CRL1162, TTD8PV, XP3NE, and XP17PV. In another embodiment, such test cells include cells isolated from patients having diseases which can be characterized by a defect in a DNA damage repair mechanism. For example, such test cells having a defect in a DNA repair mechanism include cells from patients with diseases such as Cockayne's Syndrome, trichothiodystrophy, and xeroderma pigmentosum.

In another embodiment of the present invention, a test cell has a defect in cell cycle control. According to the present invention, a defect in cell cycle control can result from cellular damage due to extrinsic or intrinsic agents. Such damage can be induced by factors such as UV light, ionizing radiation, reactive oxygen species and electrophilic alkylating agents. As used herein, cell cycle control refers to the regulation of the growth, division, and death of cells. As such, a defect in cell cycle control can be manifested at any stage in the cell cycle, including at or during the G1 phase (i.e. first growth phase), the S phase (i.e. DNA synthesis), the G2 phase (i.e. second growth phase), and/or the M phase (i.e. mitosis). A defect in cell cycle control imparts upon a test cell of the present invention the characteristic of having an enhanced transformation response in the presence of carcinogens compared to normal or wild-type cells. In addition, a defect in cell cycle control can be manifested in the cellular control of apoptosis. Apoptosis, or programmed cell death, is a mechanism employed by a cell for several purposes, including as a response to DNA damage or for inhibition of DNA synthesis. Apoptosis in response to such damage is an important means of preventing transformation of a damaged cell.

As used herein, a defect in cell cycle control includes defects in components involved in cell cycle control, and in particular, apoptosis. Such components include tumor suppressors, which typically control the cell cycle by activating genes which are capable of inhibiting or blocking cell cycle progression and inducing apoptosis. Examples of such components which are involved in cell cycle control include p53, retinoblastoma (pRB), p21, Gadd45, human single-stranded DNA binding protein (HSSB), cdk-activating kinase (CAK), cdk7, cyclin H, and cyclin A.

Test cells of the present invention having a defect in cell cycle control are known in the art and include, but are not limited to, cell lines having a defect any of the abovementioned components involved in cell cycle control. In particular, such test cells include cells selected from the group of Li-Fraumeni $p53^{mut/mut}$ fibroblasts, HL-60, RPM18402, KG-1a, RKO, CSA, BMA, NIGMS 718, NIGMS 3189, NIGMS 1526, NIGMS 3382, and HeLa cells. In another embodiment, such test cells include cells isolated from patients having diseases which are characterized by a defect in cell cycle control. For example, test cells having a defect in cell cycle control include cells from patients with diseases such as promyelocytic leukemia, lymphoid leukemia, myeloid leukemia, colorectal carcinoma, and ataxia-telangiectasia.

In yet another embodiment, a test cell of the present invention has a defect in a cellular mechanism which confers the ability to prevent damage induced by oxygen free radicals. In particular, such a defect comprises a defect in a protein involved in control of an oxidative stress response. An oxidative stress response is a cellular mechanism which protects against cellular injury due to active oxygen free radicals. In a normal cell, oxygen free radicals and other reactive oxygen species are produced as a result of oxidative stress and normal aerobic respiration, and are scavenged and detoxified to prevent damage to DNA and tissue. According to the present invention, a defect in the ability to prevent damage induced by oxygen free radicals can result from cellular damage due to extrinsic or intrinsic agents. Such damage can be induced by factors such as UV light, ionizing radiation, reactive oxygen species and electrophilic alkylating agents. A test cell having a defect in a component involved in such oxidative stress response is a particularly preferred test cell of the present invention. Components involved in response to oxidative stress include superoxide dismutase, catalase, heat shock proteins, peroxidases, glutathione peroxidase, DT diaphorase (NADH-NAD(P)H) :quinone oxidoreductase, AP-1, and NF-kB.

Test cells having a defect in the ability to prevent damage induced by oxygen free radicals are known in the art and include cells having a defect in a component involved in the oxidative stress response such as those listed above. Particularly preferred test cells having a defect in the ability to prevent damage induced by oxygen free radicals are selected from the group of NIGMS CS1AN and NIGMS GM1856. In one embodiment, test cells having a defect in the ability to prevent damage induced by oxygen free radicals include cells from patients with diseases which are characterized by such a defect. Such diseases include Cockayne's syndrome, ataxia-telangiectasia, and amylotrophic lateral sclerosis. In one embodiment, a test cell of the present invention is derived from a patient having a disease in which such disease is influenced or characterized by a defect in one of the protective cellular mechanisms described herein. Such diseases include, for example, xeroderma pigmentosum, Cockayne's syndrome, trichothiodystrophy, Fanconi's anemia, ataxia-telangiectasia, hereditary nonpolyposis colon cancer, promyelocytic leukemia, lymphoid leukemia, myeloid leukemia, colorectal carcinoma, amyotrophic lateral sclerosis, Li-Fraumeni syndrome, squamous cell carcinoma and Bloom's Syndrome.

According to the present invention, a test cell is preferably a eukaryotic cell, and more preferably, a mammalian cell. In a most preferred embodiment, a test cell of the present invention is a human cell. A test cell of the present invention can be a cell with a naturally occurring defect in an above-described protective cellular mechanism. For instance, a test cell with such a naturally occurring defect can be isolated from a patient having a disease which is characterized by a defect in a protective cellular mechanism as described above. In a further embodiment, a test cell can be engineered to have a defect in a protective cellular mechanism (i.e., such a defect is not naturally occurring). Such a cell into which a defect is engineered, or induced, can be a modified cell or a recombinant cell. In one embodiment, a modified cell includes a cell wherein a defect in a protective cellular mechanism is induced by incorporation of a portion of a virus genome into a nucleic acid molecule which encodes a protein involved in such mechanism. It is within the scope of the present invention that a cell with a naturally occurring defect in a protective cellular mechanism can additionally be modified or used as a host cell for a recombinant molecule to induce, enhance, delete, or add further defects in a protective cellular mechanism of the present invention.

As used herein, a modified cell is a cell into which a defect has been engineered or induced such that the cell is different from the cell before such manipulation (i.e. different from the normal, or wild-type cell). A modified test cell, for instance, has a genome in which a portion or portions of the test cell genome involved in a protective cellular mechanism as described herein is modified in such a way as to make the test cell more susceptible to transformation. For example, the genome of a cell which normally does not have a defect in a protective cellular mechanism as described herein can be modified to induce, or create, such a defect. Nucleic acid molecules within a normal cell can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. In one embodiment, a defective homologue of a nucleic acid molecule which encodes a protein involved in a protective cellular mechanism can be produced using a number of methods known to those skilled in the art (see, for example, Sambrook et al., 1989, *Molecular Cloning: A Laboratory Manual*, Cold Spring Harbor Labs Press.) The reference Sambrook et al., ibid., is incorporated by reference herein in its entirety. Nucleic acid mclecule homologues can be selected from a mixture of modified nucleic acids by screening for the function of the protein encoded by the nucleic acid.

A recombinant cell is a type of modified cell that is preferably produced by transfecting a host cell with one or more recombinant molecules, each comprising one or more isolated nucleic acid molecules encoding proteins involved in a protective cellular mechanism of the present invention which have a defect as described previously herein. Such a recombinant cell can include cells in which the corresponding endogenous protein involved in the protective cellular mechanism has been modified such that the endogenous protein is also defective. In another embodiment, a recombinant cell includes cells in which overexpression of an endogenous protein involved in a protective cellular mechanism by transfection with a recombinant molecule encoding such protein, even if the endogenous protein itself is not modified, results in a defect in such protective cellular mechanism.

As used herein, isolated nucleic acid molecules encoding a defective protein involved in a protective cellular mechanism are operatively linked to an expression vector containing one or more transcription control sequences. The phrase operatively linked refers to insertion of a nucleic acid molecule into an expression vector in a manner such that the molecule is able to be expressed when transfected into a host cell. As used herein, an expression vector is a DNA or RNA vector that is capable of transfecting a host cell and of effecting expression of a specified nucleic acid molecule. Preferably, the expression vector is also capable of replicating within the host cell. Expression vectors can be either prokaryotic or eukaryotic, and are typically plasmids. Expression vectors of the present invention include any vectors that function (i.e., direct gene expression) in recombinant cells of the present invention, including in mammalian cells.

The term isolated nucleic acid molecule can include an isolated natural gene which has a defect such that it encodes a defective protein involved in a protective cellular mechanism described herein, such as a protein involved in DNA repair, or a homologue thereof. Such a nucleic acid molecule can include one or more regulatory regions, full-length or partial coding regions, or combinations thereof. The minimal size of such a nucleic acid molecule is the minimal size that encodes for a protein which is involved in a protective cellular mechanism. It is to be noted that the term "a" or "an" entity refers to one or more of that entity; for example, an isolated nucleic acid molecule refers to one or more isolated nucleic acid molecules or at least one nucleic acid molecule. As such, the terms "a" (or "an"), "one or more" and "at least one" can be used interchangeably herein. It is also to be noted that the terms "comprising", "including", and "having" can be used interchangeably.

In accordance with the present invention, an isolated nucleic acid molecule is a nucleic acid molecule that has been removed from its natural milieu (i.e., that has been subject to human manipulation). For example, an isolated nucleic acid molecule can be a gene which has been separated from other genes with which it naturally occurs. As such, the term isolated does not reflect the extent to which the nucleic acid molecule has been purified. An isolated nucleic acid molecule can include DNA, RNA, or derivatives of either DNA or RNA.

An isolated nucleic acid molecule can also be produced using recombinant DNA technology (e.g., polymerase chain reaction (PCR) amplification, cloning) or chemical synthesis. Isolated nucleic acid molecules include natural nucleic acid molecules and homologies thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a protein which is involved in a protective cellular mechanism.

According to the present invention, an isolated nucleic acid molecule includes a nucleic acid sequence that encodes at least one defective protein described in the present invention. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. Proteins of the present invention include, but are not limited to, proteins having full-length naturally occurring coding regions, proteins having partial coding regions, fusion proteins, and combinations thereof.

The use of a recombinant cell, as described herein, includes the use of a recombinant vector, which comprises at least one isolated nucleic acid molecule encoding a defective protein involved in a protective cellular mechanism, which is inserted into any vector capable of delivering the nucleic acid molecule into a test cell. Such a vector contains heterologous nucleic acid sequences, that is nucleic acid sequences that are not naturally found adjacent to nucleic acid molecules encoding a defective protein, and that may be derived from a species other than the species from which the nucleic acid molecule(s) are derived. The vector can be either RNA or DNA, either prokaryotic or eukaryotic, and typically is a plasmid or a virus and preferably is a plasmid. One type of recombinant vector, referred to herein as a recombinant molecule and described in more detail below, can be used in the expression of defective proteins of the present invention.

In an assay of the present invention in which the test cell being contacted with a putative carcinogen is a recombinant cell, the recombinant cell is cultured such that the cell is capable of expressing a defective protein involved in a protective cellular mechanism as described herein, under conditions effective to produce the protein. It should be noted that such a recombinant cell may be repeatedly cloned and selected until such nucleic acid molecule or molecules have stably integrated into the host cell genome. Transfection of a nucleic acid molecule into a cell can be accomplished by any method by which a nucleic acid molecule can be inserted into the cell. Transfection techniques include, but are not limited to, electroporation, CaCl2 precipitation, microinjection, lipofection, adsorption, and protoplast fusion.

Transfected nucleic acid molecules of the present invention can remain extrachromosomal or can integrate into one or more sites within a chromosome of the transfected (i.e., recombinant) cell in such a manner that their ability to be expressed is retained. Preferably, once a host cell of the present invention is transfected with a nucleic acid molecule, the nucleic acid molecule is integrated into the host cell genome. A significant advantage of integration is that the nucleic acid molecule is stably maintained in the cell. The nucleic acid molecule can be integrated into the genome of the host cell either by random or targeted integration.

When the test cell of the present invention is a recombinant cell, suitable host cells to transfect include any cell that can be transfected with a nucleic acid molecule encoding a defective protein involved in a protective cellular mechanism, including any eukaryotic cell, and, preferably, the host cells are mammalian, and even more preferably, the host cells are human. Host cells can be either untransfected cells or cells that are already transfected with at least one nucleic acid molecule. Host cells can be any cell capable of expressing at least one protein involved in a protective cellular mechanism. Preferred host cells include fibroblasts, epithelial cells, neurons, hepatocytes, keratinocytes, hematopoietic cells and other bone marrow cells, kidney cells, and lung cells.

As used herein, recombinant molecules used in a recombinant test cell of the present invention may also (a) contain secretory signals (i.e., signal segment nucleic acid sequences) to enable an expressed protein as described herein to be secreted from the cell that produces the protein and/or (b) contain fusion sequences which lead to the expression of nucleic acid molecules encoding such proteins as fusion proteins. Recombinant molecules may include intervening and/or untranslated sequences surrounding and/or within the nucleic acid sequences of such nucleic acid molecules.

Nucleic acid molecules can be operatively linked to expression vectors containing regulatory sequences such as transcription control sequences, translation control sequences, origins of replication, and other regulatory sequences that are compatible with the recombinant cell and that control the expression of such nucleic acid molecules. In particular, recombinant molecules include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in a recombinant test cell. A variety of such transcription control sequences are known to those skilled in the art. In one embodiment, such transcription control sequences can be derived from the same source as the isolated nucleic acid molecule. Transcription control sequences can also include naturally occurring transcription control sequences naturally associated with a nucleic acid molecule prior to isolation.

It will be appreciated by one skilled in the art that use of recombinant DNA technologies can improve control of expression of transfected nucleic acid molecules by manipulating, for example, the number of copies of the nucleic acid molecules within a test cell, the efficiency with which those nucleic acid molecules are transcribed, the efficiency with which the resultant transcripts are translated, and the efficiency of post-translational modifications. Recombinant techniques useful for controlling the expression of nucleic acid molecules include, but are not limited to, integration of the nucleic acid molecules into one or more test cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the test cell, and deletion of sequences that destabilize transcripts. The activity of an expressed recombinant protein may be improved by fragmenting, modifying, or derivatizing nucleic acid molecules encoding such a protein.

In accordance with the present assay, test cells with naturally occurring defects in a protective cellular mechanism or recombinant test cells having such defects are seeded on a culture dish in medium under conditions which promote cell growth and expression of a protein involved in the transformation of cells and in the presence of a compound being tested for carcinogenicity. Effective conditions include, but are not limited to, appropriate media, temperature, pH and oxygen conditions that permit cell growth. An appropriate, or effective, medium refers to any medium in which a cell of the present invention, when cultured, is capable of cell growth and, in the case of a recombinant test cell, is capable of expression of nucleic acid molecules. Such a medium is typically a solid or liquid medium comprising growth factors and assimilable carbon, nitrogen and phosphate sources, as well as appropriate salts, minerals, metals and other nutrients, such as vitamins. Culturing is typically conducted in petri plates. Culturing is carried out at a temperature, pH and oxygen content appropriate for the test cell. Such culturing conditions are within the expertise of one of ordinary skill in the art.

The assay of the present invention includes contacting a test cell as described above with a compound being tested for carcinogenicity. For example, test cells can be grown in liquid culture medium or grown on solid medium in which the liquid medium or the solid medium contains the compound to be tested. In addition, as described above, the liquid or solid medium contains components necessary for cell growth, such as assimilable carbon, nitrogen and micronutrients.

The assay disclosed in the present invention involves contacting cells with the compound being tested for a sufficient time to allow for transformation of cells in the presence of carcinogenic compounds. The period of contact with the compound being tested can be either the entire growth phase of the assay prior to scoring or some smaller portion thereof. For example, it may be that for more toxic substances a shorter time of contact with the substance being tested is suitable. As used herein, the term "contact period" refers to the time period during which cells are in contact with the compound being tested. The term "incubation period" refers to the entire time during which cells are allowed to grow prior to scoring. Thus, the incubation period includes all of the contact period and may include a further time period during which the compound being tested is not present but during which growth is continuing prior to scoring.

The incubation time for growth of cells can vary but is sufficient to allow for the development of transformation characteristics in transformed cells. It will be recognized that shorter incubation times are preferable because compounds can be more rapidly screened for carcinogenicity. In this regard, test cells used in an assay of the present invention, under appropriate growth conditions, will develop transformation characteristics in the presence of carcinogens in preferably less than about 8 weeks, more preferably less than about 21 days, and even more preferably less than about 14 days.

After the incubation period, cell growth is scored for the presence or absence of one or more transformation characteristic. The appearance of transformed cells in the present invention, as indicated by the presence of one or more transformation characteristics, is considered to be indicative that the compound tested by the assay of the present invention is likely to be carcinogenic.

In the instance of the transformation characteristic being the formation of foci, cells can be stained and examined visually or with the aid of a microscope. The presence of foci on culture media indicates the presence of transformed cells. In a preferred embodiment of using foci formation as the transformation characteristic, test cells are grown with normal cells. As used herein, normal cells are "wild-type" cells, or cells that do not have a defect in a protective cellular mechanism as described herein. Therefore, normal cells do not have the identifying transformation characteristics as described above. In this manner, the normal cells will form a "lawn" or monolayer of contact inhibited cells. If the test compound is a carcinogen, each test cell will lose contact inhibition and grow to form a focus. If the test compound is non-carcinogenic, the test cells will be contact inhibited just as the normal cells on the lawn and only a monolayer of cells will be seen. This embodiment of the present invention provides several advantages. The normal cells function as "feeder" cells which condition the medium and metabolize the compound being tested. Further, the lawn of normal cells provides a background for comparison of transformed foci. Yet another advantage of the method is that all multi-layered aggregates of cells which overlay the lawn are counted as foci. In one embodiment, the ratio of normal cells to test cells can be between about 100:1 to about 1:1, more preferably from about 50:1 to 5:1, and most preferably about 10:1.

One advantage of the method of the present invention is that when test cells are exposed to a carcinogen, the cells develop transformation characteristics, such as formation of foci, at a rate which is considered to be statistically significantly higher than the rate at which transformation characteristics are developed in the absence of a carcinogen. More preferably, such cells develop transformation characteristics in the presence of carcinogens at a rate about 1 fold greater (i.e., 100% increase), more preferably about 25 fold greater, and most preferably about 50 fold greater than in the absence of carcinogens.

In a further embodiment of the present invention, the occurrence of transformation characteristics is proportional to the carcinogenicity of the compound being tested. That is, the assay method quantifies the carcinogenicity of the compound being tested. In this manner, the relative carcinogenic potential of two different test compounds at a given concentration can be evaluated based on the relative occurrence of transformation characteristics.

One embodiment of the present invention is a method to identify tissue-specific carcinogens. Such method includes contacting a putative tissue-specific carcinogen with a first test cell of a first tissue-type, and also with a second test cell of a second tissue-type. In this embodiment, both the first cell and the second cell have a defect in a protective cellular mechanism selected from the group of a defect in a DNA damage repair mechanism, a defect in cell cycle control and/or a defect in the ability to prevent damage induced by oxygen free radicals. An important feature of this embodiment is that the first cell and the second cell are of a different tissue-type, but have the same defect in a protective cellular mechanism as described herein. The term, "tissue-type", as used herein, is described in detail below. The method disclosed in this embodiment further comprises scoring cell growth of the first test cell and the second test cell based on a transformation characteristic as previously described herein. A positive transformation characteristic in either of the first or second test cells indicates that the compound being tested for carcinogenicity is carcinogenic. Moreover, a difference in the magnitude of a positive transformation characteristic between the first and second test cell indicates that the compound is a tissue-specific carcinogen. Identification of tissue-specific carcinogens is advantageous because the specific circumstances under which a particular carcinogen is likely to induce cellular transformation can be determined, and because the knowledge of such tissue-specificity can be particularly helpful in research and in developing preventative, diagnostic, and/or therapeutic protocols for treatment of particular diseases.

As used herein, a "tissue-specific carcinogen" refers to a carcinogen which preferentially transforms cells of a particular tissue-type over cells of another tissue-type. According to the present invention, a "tissue-type" can refer to a cell-type or, alternatively, to a tissue from a particular organ. In one embodiment, a test cell of the present invention can be of a cell-type selected from the group which includes, but is not limited to, fibroblasts, epithelial cells, neurons, hepatocytes, keratinocytes, hematopoietic cells, kidney cells, bone cells, and muscle cells. In another embodiment, a test cell of the present invention can be derived from a tissue from a particular organ, including, but not limited to, liver, bladder, uterus, bone marrow, lymph node, kidney, pancreas, skin, lung, ovary, colon, stomach, prostate, brain, thyroid, cervix, and parathyroid.

As mentioned above, in this embodiment of the present invention, an important feature is that the first test cell and the second test cell be of different tissue types, but have the same defect. For example, the first test cell could be a fibroblast having a defect in nucleotide excision repair, and the second test cell could be a lymphocyte having a defect in nucleotide excision repair (i.e., these cells are of different cell-types). In another example, the first test cell could be a skin fibroblast having a defect in nucleotide excision repair, and the second test cell could be a kidney fibroblast having a defect in nucleotide excision repair (i.e these cells are from tissues of different organs). In yet another example of this embodiment, a first test cell could be a kidney cell of any cell-type which expresses a kidney-specific protein, and the second test cell could be a lung cell of any cell-type which expresses a lung-specific protein, wherein both the first and the second test cells have a defect in nucleotide excision repair.

The method of identifying tissue-specific carcinogens can use materials as described generally herein for other methods of the present invention. As described above, a specific feature of this embodiment is that the carcinogen is evaluated for tissue-specificity by determining if there is a difference in the magnitude of a positive transformation characteristic between the first and second test cell, which indicates that the compound is a tissue-specific carcinogen. A difference in magnitude can be any measurable, statistically significant difference in a transformation characteristic between the first and second cell. Such a difference is determined based on the transformation characteristic being used in a particular assay. For example, if the transformation characteristic being scored is the formation of foci, and if, after being contacted with a putative tissue-specific carcinogen, the first test cell forms significantly more foci than the second test cell, than the carcinogen has tissue-specificity for the tissue-type of the first cell.

In preferred embodiments of the method to identify tissue-specific carcinogens, more than two test cells can be used in a given assay. For example, in a preferred embodiment, a putative carcinogen is contacted with a third test cell, wherein the third test cell is of a third, and different, tissue-type than either the first or the second test cell, but has the same defect in a protective cellular mechanism as the first and the second test cell. It is within the scope of this particular embodiment that even more cells of different tissue-types can be used in an assay (i.e., a fourth test cell of a fourth tissue-type, a fifth test cell of a fifth tissue-type, etc.).

Another embodiment of the present invention is a method to identify the biochemical mechanism of carcinogenicity of a carcinogenic compound. As used herein, the biochemical mechanism, or biochemical pathway, of carcinogenicity of a carcinogenic compound refers to the biochemical mechanism by which such a compound causes a cell to become transformed. For instance, a particular carcinogen may damage DNA in a cell by alkylating the DNA. If the cell is unable to remove or repair the alkylated DNA, it can become transformed.

A method to identify such biochemical mechanisms of carcinogenicity includes contacting a putative carcinogen with a first test cell having a defect in a first protective cellular mechanism, and also with a second test cell having a defect in a second protective cellular mechanism. In this embodiment, both the first cell and the second cell have a defect in a protective cellular mechanism which can include a defect in a DNA damage repair mechanism, a defect in cell cycle control and/or a defect in the ability to prevent damage induced by oxygen free radicals. Such defects include any of the more specific defects in a protective cellular mechanism as described previously herein. An important feature of this embodiment is that the first test cell has a defect in a different protective cellular mechanism than the defect of the second test cell.

This method further includes scoring cell growth of the first test cell and the second test cell based on a transformation characteristic as previously described herein. A positive transformation characteristic in either of the first or second test cells indicates that the compound being tested for carcinogenicity is carcinogenic. Moreover, a difference in the magnitude of a positive transformation characteristic between the first and second test cell indicates that the biochemical mechanism of the carcinogen is associated with a specific defect in a protective cellular mechanism. In other words, if the first test cell becomes transformed in the absence of (or significantly lesser presence of) a transformation characteristic in the second test cell, this result would indicate that the biochemical mechanism of carcinogenicity of the carcinogen being tested is associated with the defect in the protective cellular mechanism of the first test cell and not with the defect of the second test cell.

An example of such a method to identify the biochemical mechanism of carcinogenicity of a compound is described as follows. A first test cell could be a test cell from a patient with Fanconi's anemia which has a defect in the ability to repair DNA damage due to crosslinking, and a second test cell could be a cell from a patient with xeroderma pigmentosum (XP) which has a defect in the ability to repair DNA damage due to alkylation. A transformation characteristic of a greater magnitude observed with the first test cell (Fanconi's anemia cell) than is observe, with the second test cell (XP cell), indicates that the biochemical mechanism of carcinogenicity is by crosslinking of DNA. On the other hand, a transformation characteristic of a greater magnitude observed with the second test cell (XP cell) than is observed with the first test cell (Fanconi's anemia cell), indicates that the biochemical mechanism of carcinogenicity is by alkylation of DNA.

The method of identifying the biochemical mechanism of carcinogenicity of a compound can use materials as described generally herein for other methods of the present invention. As previously described herein, a difference in the magnitude of a transformation characteristic between a first and second cell can be any measurable, statistically significant difference in a transformation characteristic between the first and second cell. Moreover, it is within the scope of this embodiment that more than two test cells can be used in a given assay. For example, in a preferred embodiment, a putative carcinogen is contacted with a third test cell having a defect in a third, and different, protective cellular mechanism than either the first or the second test cell. It is within the scope of this particular embodiment that even more cells having a defect in different protective cellular mechanisms can be used in an assay.

A further aspect of the present invention is a method to identify anti-carcinogenic agents. This method can use materials as described generally herein for other methods of the present invention. The method to identify anti-carcinogenic agents (i.e., transformation inhibitors) can involve the use of test cells which comprise a defect in a protective cellular mechanism selected from a defect in a DNA damage repair mechanism, a defect in cell cycle control, and/or a defect in the ability to prevent damage induced by oxygen free radicals, as described in detail above. In one embodiment, this method includes contacting such a test cell with a known carcinogen. Such a carcinogen can be either a genotoxic or nongenotoxic carcinogen. This method further includes contacting such a test cell in the presence of a carcinogen with a compound to be evaluated for its effectiveness as an anti-carcinogenic agent. Such a cell is contacted with both a carcinogen and a compound to be tested in the manner as noted above for other methods of the present invention. After a suitable incubation period, cell growth is scored for the presence or absence of one or more transformation indicators as noted above.

In another embodiment of the method to identify anticarcinogenic compounds, a test cell as described above, which has the phenotype of being transformed in the absence of a known carcinogen is used. Such cells have one or more of the transformation characteristics discussed above.

The absence of a transformation characteristic or a reduction in the incidence of transformation characteristics compared to the rate of occurrence of transformation characteristics in the absence of the compound being tested, is an indication that the compound being tested is effective as an anti-carcinogenic agent.

Carcinogens which can be used in this embodiment of the present invention can be any known carcinogen, such as aflatoxin B, 3-methylcholanthrene, benzo[a]pyrene and 4-aminobiphenyl. Alternatively, carcinogens can be any other known carcinogen or carcinogens identified in the future.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiment described hereinabove is further intended to explain the best mode presently known of practicing the invention and to enable others skilled in the art to utilize the invention as such, or other embodiments, and with the various modifications required by their particular application or uses of the invention. It is intended that the appended claims be construed to include alternative embodiments to the extent permitted by the prior art.

What is claimed is:

1. A method to evaluate the anticarcinogenicity of a compound, said method comprising:

(a) contacting a test cell having a defect selected from the group consisting of a defect in a DNA damage repair mechanism, a defect in cell cycle control, and a defect in the ability to prevent damage induced by oxygen free radicals, with said compound being tested for anticarcinogenicity under conditions which in the absence of said compound, said test cell is transformed; and (b) scoring cell growth of said test cell based on a phenotype transformation characteristic, wherein the absence or reduction of a transformation characteristic indicates that said compound is anticarcinogenic.

2. The method of claim 1, wherein said conditions comprise said test cell being contacted by said compound being tested for anticarcinogenicity in the presence of a known carcinogen.

3. The method of claim 1, wherein said test cell has the phenotype of being transformed under said conditions in the absence of a known carcinogen.

* * * * *